US012714492B2

(12) United States Patent
Cui et al.

(10) Patent No.: US 12,714,492 B2
(45) Date of Patent: Aug. 25, 2026

(54) DATA ADJUSTMENT METHOD IN RADIO FREQUENCY OPERATION AND RADIO FREQUENCY HOST

(71) Applicant: HANGZHOU BRONCUS MEDICAL CO., LTD., Hangzhou (CN)

(72) Inventors: Changjie Cui, Hangzhou (CN); Hong Xu, Hangzhou (CN)

(73) Assignee: Hangzhou Broncus Medical Co., Ltd., Hangzhou (CN)

( * ) Notice: Subject to any disclaimer, the term of this patent is extended or adjusted under 35 U.S.C. 154(b) by 312 days.

(21) Appl. No.: 18/346,060

(22) Filed: Jun. 30, 2023

(65) Prior Publication Data

US 2023/0338079 A1 Oct. 26, 2023

Related U.S. Application Data

(63) Continuation of application No. PCT/CN2021/142754, filed on Dec. 29, 2021.

(30) Foreign Application Priority Data

Dec. 31, 2020 (CN) ......................... 202011640205.8

(51) Int. Cl.
*A61B 18/14* (2006.01)
*A61B 18/00* (2006.01)
*H04W 52/06* (2009.01)

(52) U.S. Cl.
CPC ............. *A61B 18/14* (2013.01); *H04W 52/06* (2013.01); *A61B 2018/00577* (2013.01);
(Continued)

(58) Field of Classification Search
CPC .......... A61B 18/14; A61B 2018/00577; A61B 2018/00648; A61B 2018/00702;
(Continued)

(56) References Cited

U.S. PATENT DOCUMENTS

2003/0060818 A1 3/2003 Kannenberg et al.
2012/0123400 A1 5/2012 Francischelli et al.
(Continued)

FOREIGN PATENT DOCUMENTS

CN 106137381 11/2016
CN 109589169 4/2019
(Continued)

OTHER PUBLICATIONS

International Search Report and Written Opinion, issued in the corresponding PCT application No. PCT/CN2021/142754, dated Mar. 10, 2022, 16 pages (translation enclosed).
(Continued)

*Primary Examiner* — Beverly M Flanagan

(57) ABSTRACT

A data adjustment method in a radio frequency operation is provided, which includes providing radio frequency signals with a preset power value and outputting the radio frequency signals to a radio frequency probe; detecting physical characteristic data of an object of a present radio frequency operation in real time; determining a power adjustment algorithm according to the type of the radio frequency probe when the physical characteristic data exceeds the preset range, calculating a target power value according the power adjustment algorithm and adjusting the radio frequency output power to the target power value; and adjusting the preset range according to the physical characteristic data detected in real time in a preset period of time before a present moment when the physical characteristic data does not exceed the preset range.

17 Claims, 3 Drawing Sheets

(52) U.S. Cl.
CPC ............... *A61B 2018/00648* (2013.01); *A61B 2018/00702* (2013.01); *A61B 2018/00791* (2013.01); *A61B 2018/00875* (2013.01)

(58) Field of Classification Search
CPC ........... A61B 2018/00791; A61B 2018/00875; A61B 2018/00642; A61B 2018/00636; A61B 2018/00666; A61B 2018/00684; A61B 2018/00678; H04W 52/06
USPC ............................................................ 606/33
See application file for complete search history.

(56) References Cited

U.S. PATENT DOCUMENTS

| | | | | |
|---|---|---|---|---|
| 2017/0105783 | A1 | 4/2017 | Highsmith et al. | |
| 2020/0352635 | A1* | 11/2020 | Batchelor .......... | A61B 18/1445 |

FOREIGN PATENT DOCUMENTS

| | | | |
|---|---|---|---|
| CN | 109589169 | A | 4/2019 |
| CN | 110074857 | | 8/2019 |
| CN | 111214288 | | 6/2020 |
| CN | 112773497 | | 5/2021 |
| CN | 112807071 | | 5/2021 |
| CN | 112821898 | | 5/2021 |
| EP | 3202355 | A1 | 8/2017 |
| WO | 2020227519 | A1 | 11/2020 |

OTHER PUBLICATIONS

First Chinese Office Action and Search Report, issued in the corresponding Chinese patent application No. 202011640205.8, dated Oct. 21, 2021, 30 pages (translation enclosed).

Office Action Dated Mar. 26, 2025 for Corresponding Indian Patent Application No. 202327048563.

The extended European search report Issued on Oct. 30, 2024 for Corresponding European Patent Application No. 21914575.2.

Office Action Issued on Jun. 4, 2024 for Corresponding Japanese Patent Application No. 2023-540504.

Office Action Issued on May 29, 2025 for Corresponding Korean Patent Application No. 10-2023-7026137.

Office Action Issued on Feb. 26, 2026 for Corresponding Korean Patent Application No. 10-2023-7026137.

* cited by examiner

DATA ADJUSTMENT METHOD IN RADIO FREQUENCY OPERATION AND RADIO FREQUENCY HOST

CROSS-REFERENCE TO RELATED APPLICATIONS

The present application is a Continuation Application of PCT Application No. PCT/CN2021/142754, filed on Dec. 29, 2021, which claims the priority of Chinese Application No. 202011640205.8, filed on Dec. 31, 2020, the entire contents of which are hereby incorporated by reference.

TECHNICAL FIELD

Embodiments of the present disclosure relate to the field of electronic technology, and particularly to a data adjustment method in a radio frequency operation and a radio frequency host.

DESCRIPTION OF THE PRIOR ART

In the radio frequency technology, a radio frequency operation is performed accurately applying radio frequency energy to an object by a radio frequency host under the guidance of an image. In the radio frequency operation, the operation effect needs to be ensured, while care is taken to protect the object and operator from damage and injury.

In the prior art, during the operation of the radio frequency host, since the physical characteristics of the object keep changing due to the action of radio frequency energy, safety problems will be caused to the object or operator, or the radio frequency operation effect is caused to be unsatisfactory, if constant parameters are used to carry out the radio frequency operation.

SUMMARY OF THE DISCLOSURE

An embodiment of the present disclosure provides a data adjustment method in a radio frequency operation and a radio frequency host. During the radio frequency operation, the output power of radio frequency signals or a preset range for physical characteristic data of an object of the radio frequency operation is adjusted, to improve the safety and effectiveness of the radio frequency operation.

In an aspect, an embodiment of the present disclosure provides a data adjustment method in a radio frequency operation, which includes: providing radio frequency signals with a preset power value, and outputting the radio frequency signals to a radio frequency probe; detecting physical characteristic data of an object of a present radio frequency operation in real time, and determining whether the physical characteristic data exceeds a preset range; and when the physical characteristic data exceeds the preset range, determining a power adjustment algorithm according to the type of the radio frequency probe, calculating a target power value according to the power adjustment algorithm, and adjusting the radio frequency output power to the target power value; and when the physical characteristic data does not exceed the preset range, adjusting the preset range according to the physical characteristic data detected in real time in a preset period of time before a present moment.

In an aspect, an embodiment of the present disclosure further provides a radio frequency host, which includes: an output module, configured to provide radio frequency signals with a preset power value, and output the radio frequency signals to a radio frequency probe; a detection module, configured to detect physical characteristic data of an object of a present radio frequency operation in real time, and determine whether the physical characteristic data exceeds a preset range; and an adjustment module, configured to determine a power adjustment algorithm according to the type of the radio frequency probe, calculate a target power value according to the power adjustment algorithm, and adjust the radio frequency output power to the target power value. The adjustment module is further configured to adjust, when the physical characteristic data does not exceed the preset range, the preset range according to the physical characteristic data detected in real time in a preset period of time before a present moment.

In an aspect, an embodiment of the present disclosure further provides a radio frequency host, which includes a memory and a processor. The memory stores executable program codes; and the processor is coupled to the memory, and configured to invoke the executable program codes stored in the memory, and implement the data adjustment method in a radio frequency operation as described above.

As can be known from the above embodiments of the present disclosure, the radio frequency signals are provided with a preset power value, and the radio frequency signals are outputted to a radio frequency probe. The physical characteristic data of the object of the radio frequency operation is detected in real time during the radio frequency operation, and whether the physical characteristic data exceeds the preset range is determined. The power adjustment algorithm is determined according to the type of the radio frequency probe when the physical characteristic data exceeds the preset range, the target power value is calculated according to the power adjustment algorithm, and the radio frequency output power is adjusted to the target power value, to reduce the risk of the radio frequency operation damaging the object and improve the safety of the radio frequency operation. When the physical characteristic data does not exceed the preset range, the preset range of the physical characteristic data is adjusted, and the reasonableness of the preset range is improved by automatically updating the preset range, to provide a more accurate data basis for subsequent radio frequency operations, and improve the reasonableness and success rate of the radio frequency operation.

BRIEF DESCRIPTION OF DRAWINGS

In order to describe the technical solutions according to the embodiments of the present disclosure or in the prior art more clearly, the drawings needed to be used in the embodiments or in the prior art will be described briefly below. Apparently, the drawings in the following description show some embodiments of the present disclosure. Other drawings can be obtained by persons of ordinary skill in the art based on these drawings without creative efforts.

DESCRIPTION OF EMBODIMENTS

In order to make the objects, technical solutions and advantages of the embodiments of the present disclosure clearer, the technical solutions according to the embodiments of the present disclosure will be clearly and completely described below with reference to drawings in the embodiments of the present disclosure. Apparently, the embodiments described are merely some embodiments, but not all of the embodiments of the present disclosure. All other embodiments obtained by ordinary persons skilled in the art based on the embodiments of the present disclosure without creative efforts shall fall within the protection scope of the present disclosure.

Figure 1:
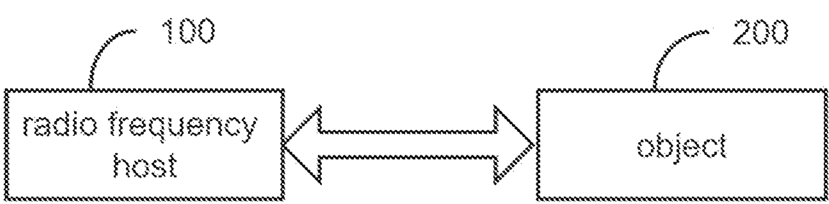
FIG. 1 is a schematic diagram showing an application scenario of a data adjustment method in a radio frequency operation according to an embodiment of the present disclosure.

FIG. 1 is a schematic diagram showing an application scenario of a data adjustment method in a radio frequency operation according to an embodiment of the present disclosure. The data adjustment method in a radio frequency operation includes: during the radio frequency operation, outputting radio frequency signals at a set power, detecting physical characteristic data of an object of the radio frequency operation in real time, and determining whether to adjust the output power of the radio frequency signals or the physical characteristic data according to the change of the physical characteristic data. As a result, the data of the radio frequency operation tends to be more reasonable, thereby improving the success rate and safety of the radio frequency operation.

Particularly, an implementation body of the data adjustment method is a radio frequency host that may be specifically a radio frequency ablation instrument among other devices. As shown in FIG. 1, a radio frequency host 100 is connected to an object 200, and then a radio frequency operation is started. The radio frequency host 100 has a radio frequency probe, and the radio frequency host 100 transmits radio frequency signals with a preset frequency by a radio frequency signals module, which signals are acted on the object 200 by the radio frequency probe. In the radio frequency operation, as the nature of the object 200 changes, physical characteristic data also changes. The object 200 can be any object that needs the radio frequency operation. For example, when the radio frequency host 100 is a radio frequency ablation instrument, the object 200 can be an organism with an abnormal tissue in the body that needs to be ablated.

The radio frequency host 100 has an input interface that can be externally connected to a movable memory such as U disk, or externally connected to an input device such as keyboard and mouse, to read data from the removable memory, or acquire data inputted by a user from the input device. Alternatively, the radio frequency host 100 may be connected to a server over a network, through the server, big data from all radio frequency hosts connected to the server can be obtained. The big data includes various historical data related to the radio frequency operation.

Figure 2:
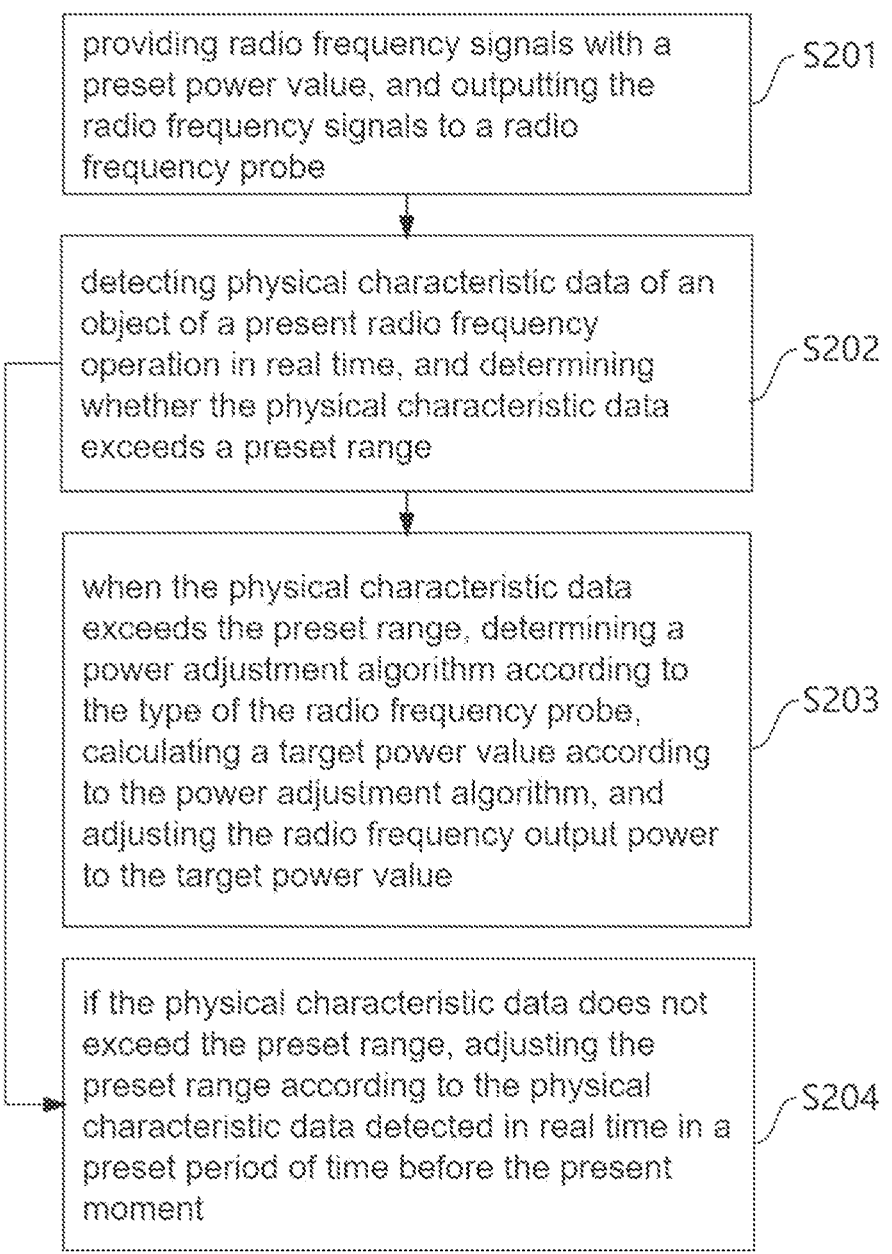
FIG. 2 is a schematic flow chart of a data adjustment method in a radio frequency operation according to an embodiment of the present disclosure.

FIG. 2 is a schematic flow chart of a data adjustment method in a radio frequency operation according to an embodiment of the present disclosure. The method is applicable to the radio frequency host as shown in FIG. 1. As shown in FIG. 2, the method specifically includes the following steps:

Step S201: providing radio frequency signals with a preset power value, and outputting the radio frequency signals to a radio frequency probe.

Particularly, the preset power value can be obtained from historical radio frequency operation data of all radio frequency hosts in a network obtained by a server, or obtained from set data inputted into the radio frequency host by a user.

S202: detecting physical characteristic data of an object of a present radio frequency operation in real time, and determining whether the physical characteristic data exceeds a preset range.

The physical characteristic data includes the temperature and the impedance of the object. The temperature or the impedance is detected in real time, or both the temperature and the impedance are detected simultaneously.

In the radio frequency operation, the radio frequency signals outputted on the object have radio frequency energy, and the physical characteristic data of a site where the radio frequency operation is performed will change under the action of the radio frequency energy.

The preset range is a numerical range defined by a minimum value and a maximum value, and the way of obtaining the minimum value and the maximum value is the same as the way of obtaining the set power data in Step S201. That is, the minimum value and the maximum value can be obtained from historical radio frequency operation data of all radio frequency hosts in a network obtained by a server, or obtained from set data inputted into the radio frequency host by a user.

A preset range of the temperature value is a preset temperature range, and a preset range of the impedance value is a preset impedance range.

S203: when the physical characteristic data exceeds the preset range, determining a power adjustment algorithm according to the type of the radio frequency probe, calculating a target power value according to the power adjustment algorithm, and adjusting the radio frequency output power to the target power value.

When the physical characteristic data is greater than the maximum value of the preset range, or less than the minimum value of the preset range, it is determined to exceed the preset range. Then, the output power of the radio frequency signals is adjusted, to reduce or increase the physical characteristic data. Particularly, when the temperature value of the object is greater than the maximum value of the preset temperature range, or the impedance value of the object is greater than the maximum value of the preset impedance range, the output power is reduced to a first target power value, so as to reduce the temperature value or the impedance value. When the temperature value of the object is less than the minimum value of the preset temperature range, or the impedance value of the object is less than the minimum value of the preset impedance range, the output power is increased to a second target power value, so as to increase the temperature value or the impedance value.

The type of the radio frequency probe includes a single-electrode radio frequency probe and a multi-electrode radio frequency probe, and a different type of probe corresponds to a different power adjustment algorithm. Particularly, the algorithm corresponding to the single-electrode radio frequency probe is to obtain the target power value by querying a preset corresponding relationship between the power adjustment amount and the variation of the physical characteristic data; and the algorithm corresponding to the multi-electrode radio frequency probe is the PID algorithm, and the target power value is calculated by the preset PID algorithm.

S204: if the physical characteristic data does not exceed the preset range, adjusting the preset range according to the physical characteristic data detected in real time in a preset period of time before the present moment.

If the physical characteristic data does not exceed the preset range, the preset range is adjusted according to the physical characteristic data detected in real time in a preset period of time before a present moment. The adjusted physical characteristic data can be used as historical radio frequency operation data, and set as a data basis for a preset range of the physical characteristic data of a next radio frequency operation, thus making the data be of great referential value, and improving the accuracy of the radio frequency operation.

In the embodiment of the present disclosure, the radio frequency signals are provided with a preset power value, and the radio frequency signals are outputted to the radio frequency probe. Physical characteristic data of the object of the radio frequency operation is detected in real time during the radio frequency operation, and whether the physical characteristic data exceeds a preset range is determined. The power adjustment algorithm is determined according to the type of the radio frequency probe when the physical characteristic data exceeds the preset range, the target power value is calculated according to the power adjustment algorithm, the radio frequency output power is adjusted to the target power value, and then the radio frequency signals are outputted, reducing the risk of the radio frequency operation damaging the object and improving the safety of the radio frequency operation. When the physical characteristic data does not exceed the preset range, the preset range of the physical characteristic data is adjusted, improving the reasonableness of the preset range by automatically updating the preset range, to provide a more accurate data basis for subsequent radio frequency operations, and improve the reasonableness and success rate of the radio frequency operation.

Figure 3:
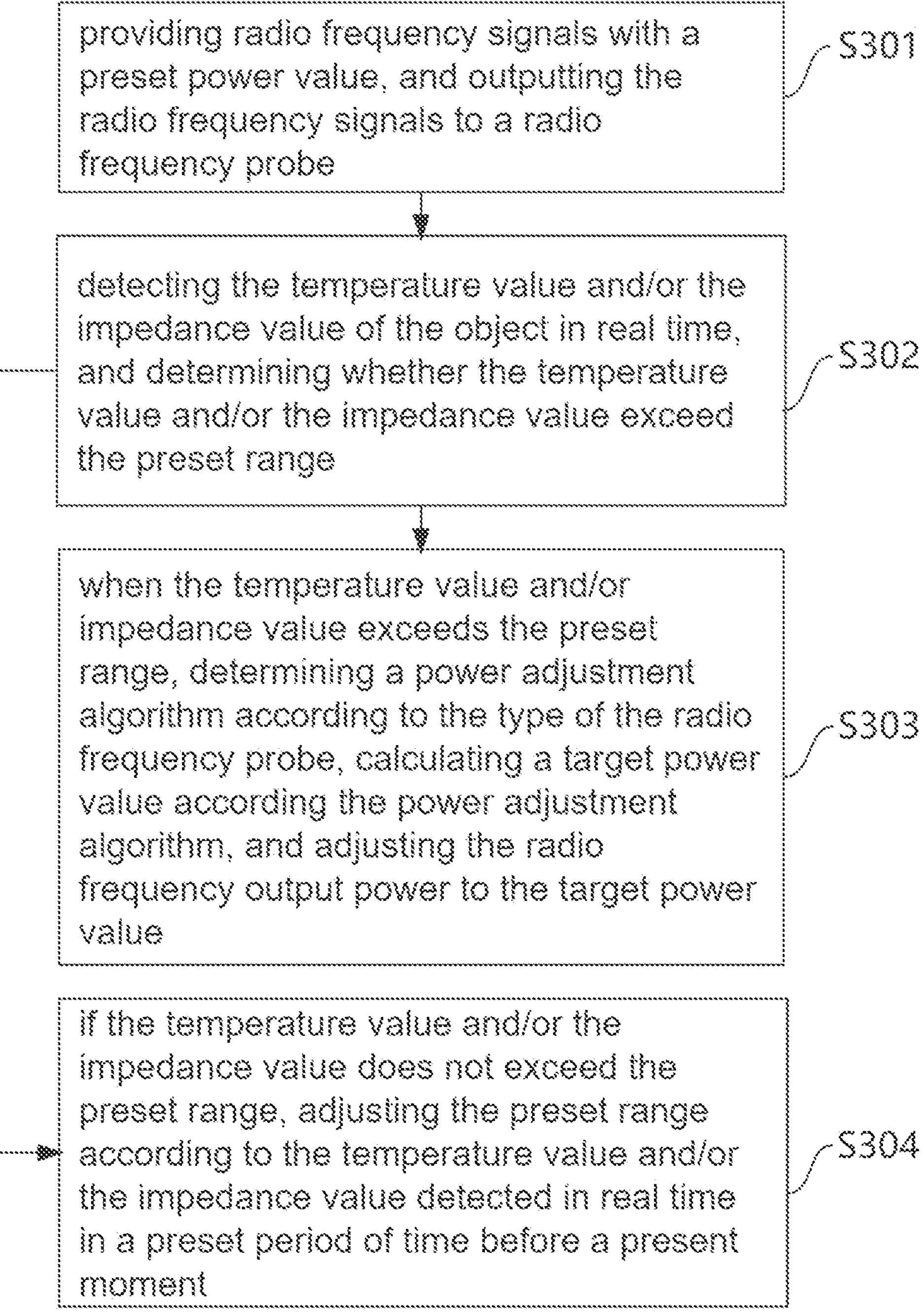
FIG. 3 is a schematic flow chart of a data adjustment method in a radio frequency operation according to another embodiment of the present disclosure.

FIG. 3 is a schematic flow chart of a data adjustment method in a radio frequency operation according to another embodiment of the present disclosure. The method is applicable to the radio frequency host as shown in FIG. 1. As shown in FIG. 3, the method specifically includes the following steps:

Step S301: providing radio frequency signals with a preset power value, and outputting the radio frequency signals to a radio frequency probe.

Particularly, the set power data can be obtained through the following two manners.

In a first manner, the set power data can be obtained from the historical radio frequency operation data corresponding to the task and object of the radio frequency operation obtained from a server. The historical radio frequency operation data is classified according to the task of the radio frequency operation and the nature of the object. For example, the historical radio frequency operation data of task No. 1 performed on object A is classified into one category, the historical radio frequency operation data of task No. 2 performed on object A is classified into one category, the historical radio frequency operation data of task No. 1 performed on object B is classified into one category, and the like. With the same task and the same nature of the object, the respective category of historical radio frequency operation data corresponds to the same radio frequency operation time.

Therefore, when the radio frequency operation is performed, the radio frequency power data of the historical radio frequency operation data corresponding to the task and object of the present radio frequency operation is acquired, the acquired radio frequency power data is used as the set power data, the output power of the radio frequency signals in various periods of time of the radio frequency operation is set according to the corresponding relationship between the set power data and the radio frequency operation time, and the radio frequency signals having the output power is outputted to the object. Particularly, the output power value of the radio frequency signals in the historical radio frequency operation data is determined as the set power data, and the set power data is specifically a change trend curve representing the corresponding relationship between the radio frequency operation time and the output power. From the change trend curve, the output power value corresponding to the operation time in the period of the present radio frequency operation is acquired, and the acquired output power value is set as the output power of the radio frequency signals.

In a second manner, the set power data can be obtained from the set data inputted into the radio frequency host by a user. Particularly, the set power data is acquired from the set data in the removable memory connected to the radio frequency host, or the set power data is acquired from the set data inputted via an input device of the radio frequency host. The set power data is a numerical range including a maximum value of the set power and a minimum value of the set power.

A median value of the numerical range is set as the output power of the radio frequency signals. The radio frequency signals having the output power is outputted to the object.

Step S302: detecting the temperature value and/or the impedance value of the object in real time, and determining whether the temperature value and/or the impedance value exceed the preset range.

Step S303: when the temperature value and/or the impedance value exceeds the preset range, determining a power adjustment algorithm according to the type of the radio frequency probe, calculating a target power value according the power adjustment algorithm, and adjusting the radio frequency output power to the target power value.

When the type of the radio frequency probe is a single-electrode radio frequency probe, the power adjustment algorithm is to obtain the target power value by querying a preset corresponding relationship between the power adjustment amount and the variation of the physical characteristic data. Particularly, the variation of the physical characteristic data is an adjustment value of the temperature value or the impedance value of the object.

When the temperature value or the impedance value of the object detected in real time exceeds the preset range, the target value is determined in the preset range, and the adjustment value of the temperature value or the impedance value is calculated from the target value and the temperature value or the impedance value. The power adjustment value is obtained by querying the corresponding relationship between the power adjustment value and the adjustment value of the temperature value or the impedance value.

When the temperature value or the impedance value is greater than the maximum value of the preset range, the power adjustment value is subtracted from the preset power value to obtain a first target power value. The radio frequency output power is reduced to the first target power value, and then the radio frequency signals are outputted. When the temperature value or the impedance value is less than the minimum value of the preset range, the preset power value is added with the power adjustment amount to obtain a second target power value. The radio frequency output power is increased to the second target power value, and then the radio frequency signals are outputted.

When the radio frequency probe of the radio frequency host is a multi-electrode radio frequency probe, the power adjustment algorithm is the preset Proportional Integral Differential (PID) algorithm, by which the target power value is calculated. Particularly, if the temperature value or the impedance value of the object detected in real time is greater than the maximum value of the preset range, the total to-be-set power is determined according to the minimum impedances of the electrodes of the multi-electrode radio frequency probe, and the real-time total power of the radio frequency probe of the radio frequency host is detected. The power adjustment value is calculated by the preset PID algorithm according to the total to-be-set power and the real-time total power, and the target power is calculated according to the power adjustment value and the present output power of the radio frequency signals. Then, the radio frequency output power is reduced to the target power.

Particularly, the impedances of multiple electrodes of the multi-electrode radio frequency probe are detected, and the individual electrode with the smallest impedance is determined. The total to-be-set power is calculated according to the power of the individual electrode, and the total to-be-set power is the upper limit of the power of the electrodes.

The power calculation formula is $P=U^2/R$. Since the electrodes of the multi-electrode radio frequency probe are connected to the same voltage output, the electrodes have the same voltage at the site of the radio frequency operation. The power of each electrode depends on the impedance R, and the power P increases with the decrease of R. The power of each individual electrode is delimited by the set total power, and can be equal to, but cannot exceed the set total power. The set total power is the sum of the powers of the electrodes.

Particularly, the present total to-be-set power is calculated according to the impedances of the electrodes.

According to the formula $P=U^2/R$, it can be deduced that the relationship between the power $P_{lim}$ of the electrode with the smallest impedance and the power $P_n$ of other individual electrodes is:

$$\frac{P_{lim}}{P_n} = \frac{U^2/R_{lim}}{U^2/R_n} = \frac{R_n}{R_{lim}},$$

where that is, $$P_n = \frac{P_{lim}R_{lim}}{R_n}.$$

$P_{lim}$ is a known power of the electrode with the smallest impedance, and according to $R_{lim}$ and the impedances $R_n$ of other individual electrodes, $P_n$ corresponding to the other individual electrodes can be obtained. The total to-be-set power P can be calculated by the formula $$P = \sum_{i=1}^{n} P_i.$$

According to the currently measured real-time total power and the total to-be-set power P, the total power increment ΔP can be obtained according to the PID algorithm. The PID algorithm is accomplished by $$u(k) = K_P\left\{err(k) + \frac{T}{T_I}\sum_{j=0}^{k} err(j) + \frac{T_D}{T}[err(k) - err(k-1)]\right\}; \quad \text{Formula 1}$$

$$\text{or } u(k) = K_P err(k) + K_I\sum_{j=0}^{k} err(j) + K_D[err(k) - err(k-1)]; \quad \text{Formula 2}$$

$$\text{wherein } K_P,\ K_I = K_P\frac{T}{T_I} \text{ and, } K_D = K_P\frac{T_D}{T}$$

are respectively the proportional coefficient, integral coefficient and differential coefficient of the PID algorithm, T is the sampling time, $T_I$ is the integration time (also referred to as the integral coefficient), $T_D$ is the differential time (also referred to as the differential coefficient), err(k) is the difference between the total to-be-set power and the real-time total power, and u(k) is the output.

By using the incremental PID algorithm ΔP=u(k)−u(k−1), it can be obtained from Formula 2 above:

$$\Delta P = K_P[err(k) - err(k-1)] + K_I err(k) + K_D[err(k) - 2err(k-1) + err(k-2)]$$

The output adjustment amount is calculated according to ΔP. The adjustment amount has a one-to-one mapping relationship with ΔP, because the power adjustment is achieved by controlling voltage signals from a power board, the output voltage corresponds to input digital signals of a digital-to-analog converter, and the adjustment amount actually corresponds to the digital signals. The mapping relationship refers to a corresponding relationship between the output and ΔP. For example, the output of 1 means that the corresponding power increment ΔP is 0.1 w. In this way, the control of ΔP is achieved according to the mapping relationship.

The current power value is increased by a value of ΔP to obtain the target power value. When ΔP is a negative value, the increment ΔP means to reduce the radio frequency output power, to lower the temperature. Otherwise, when ΔP is a negative value, it means to increase the radio frequency output power, to increase the temperature.

The radio frequency output power is adjusted to the target power and then the radio frequency signals are outputted.

If the temperature value or the impedance value of the object detected in real time is less than the minimum value of the preset range, the power is adjusted in the way of that has described above.

Step S304: if the temperature value and/or the impedance value does not exceed the preset range, adjusting the preset range according to the temperature value and/or the impedance value detected in real time in a preset period of time before a present moment.

Particularly, according to the various temperature values and/or the impedance values detected in real time in the preset period of time, and a preset selection algorithm, target values are selected from the various temperature values and/or the impedance values in the preset period of time to update the extreme values of the preset range. The extreme values include a minimum and a maximum value.

More specifically, the preset period of time is 10 sec. Taking temperature as an example, a minimum value among various temperature values in 10 seconds before the present moment is selected as the minimum value of the preset range, and a maximum value among various temperature values is selected as the maximum value of the preset range.

Alternatively, a median value of various temperature values in 10 seconds before the present moment is calculated, and the to-be-updated extreme values corresponding to the median value is calculated according to the median value with reference to the difference between the median value and the extreme values of the preset range before updating. The calculated extreme values are the extreme values of the updated preset range.

In the embodiment of the present disclosure, set power data corresponding to a radio frequency operation is acquired, an output power of the radio frequency signals is set according to the set power data, and then the radio frequency signals are outputted. The temperature value and/or the impedance value of the object of the radio frequency operation are detected in real time during the radio frequency operation, and whether the temperature value and/or the impedance value exceeds a preset range is determined. A power adjustment algorithm is determined according to the type of the radio frequency probe when the temperature value and/or the impedance value exceeds the preset range, and a target power value is calculated according to the power adjustment algorithm. If the temperature value or the impedance value is greater than the maximum value of the preset range, the radio frequency output power is reduced to the target power value, to reduce the risk of the radio frequency operation damaging the object and improve the safety of the radio frequency operation. If the temperature value or the impedance value is less than the minimum value of the preset range, the radio frequency output power is increased to the target power value, to improve the effect of the radio frequency operation. Further, if the temperature value and/or the impedance value does not exceed the preset range, the preset range of the temperature value and/or the impedance value is adjusted, improving the reasonableness of the preset range by automatically updating the preset range, to provide a more accurate data basis for subsequent radio frequency operations, and improve the reasonableness and success rate of the radio frequency operation.

Figure 4:
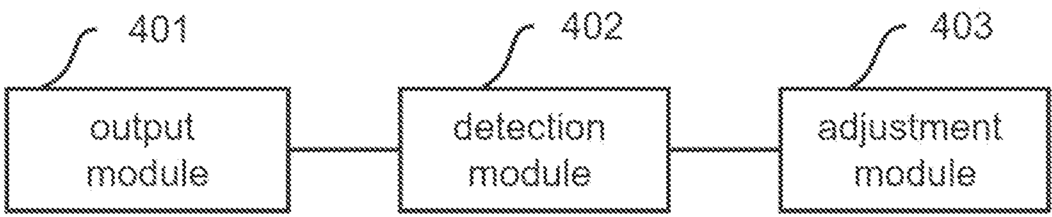
FIG. 4 is a schematic diagram of a radio frequency host according to an embodiment of the present disclosure.

FIG. 4 is a schematic diagram of a radio frequency host according to an embodiment of the present disclosure. For illustration, only the parts relevant to the embodiment of the present disclosure are shown. The radio frequency host is a radio frequency host for implementing the data adjustment method in a radio frequency operation described in the above embodiments. The radio frequency host includes:

- an output module 401, configured to provide radio frequency signals with a preset power value, and output the radio frequency signals to a radio frequency probe;
- a detection module 402, configured to detect physical characteristic data of an object of a present radio frequency operation in real time, and determine whether the physical characteristic data exceeds a preset range; and
- an adjustment module 403, configured to determine a power adjustment algorithm according to the type of the radio frequency probe, calculate a target power value according the power adjustment algorithm, and adjust the radio frequency output power to the target power value.

The adjustment module 403 is further configured to adjust the preset range according to the physical characteristic data detected in real time in a preset period of time before a present moment if the physical characteristic data does not exceed the preset range.

Through the various modules in the radio frequency host, the radio frequency signals are provided with a preset power value, and the radio frequency signals are outputted to the radio frequency probe; physical characteristic data of the object of the radio frequency operation is detected in real time during the radio frequency operation, and whether the physical characteristic data exceeds a preset range is determined; the power adjustment algorithm is determined according to the type of the radio frequency probe when the physical characteristic data exceeds the preset range, the target power value is calculated according to the power adjustment algorithm, and the output power of the radio frequency signals is adjusted to the target power and then the radio frequency signals are outputted, to reduce the risk of the radio frequency operation damaging the object and improve the safety of the radio frequency operation. If the physical characteristic data does not exceed the preset range, the preset range of the physical characteristic data is adjusted, and the reasonableness of the preset range is improved by automatically updating the preset range, to provide a more accurate data basis for subsequent radio frequency operations, and improve the reasonableness and success rate of the radio frequency operation.

Further, the adjustment module 403 is further configured to acquire, when the type of the radio frequency probe is a single-electrode radio frequency probe, the target power value by a power adjustment algorithm by querying a preset corresponding relationship between the power adjustment amount and the variation of the physical characteristic data; and

- calculate the target power value by a power adjustment algorithm that is the preset PID algorithm if the type of the radio frequency probe is a multi-electrode radio frequency probe.

Further, the detection module 402 is further configured to detect the temperature value and/or the impedance value of the object in real time.

Further, the variation of the physical characteristic data is an adjustment value of the temperature value or the impedance value of the object.

The adjustment module 403 is further configured to determine the target value in the preset range when the temperature value or the impedance value of the object detected in real time exceeds the preset range, calculate the adjustment value of the temperature value or the impedance value according to the target value and the temperature value or the impedance value;

- obtain the power adjustment value by querying the corresponding relationship between the power adjustment value and the adjustment value of the temperature value or the impedance value;
- subtract the power adjustment value from the preset power value to obtain a first target power value if the temperature value or the impedance value is greater than the maximum value of the preset range, and reduce the radio frequency output power to the first target power value; and
- add the preset power value with the power adjustment amount to obtain a second target power value if the temperature value or the impedance value is less than the minimum value of the preset range, and increase the radio frequency output power to the second target power value.

The output module 401 is further configured to output the radio frequency signals with a radio frequency output power adjusted to the first target power value or the second target power value.

When the radio frequency probe of the radio frequency host is a multi-electrode radio frequency probe, the adjustment module 403 is further configured to determine the total to-be-set power according to the minimum impedance of the electrodes of the multi-electrode radio frequency probe, if the temperature value or the impedance value of the object detected in real time is greater than the maximum value of the preset range; and detect the real-time total power of the radio frequency probe.

The adjustment module 403 is further configured to calculate a power adjustment value by a preset PID algorithm according to the total to-be-set power and the real-time total power, calculate a target power value according to the power adjustment value and the present output power of the radio frequency signals, and reduce the output power of the radio frequency signals to the target power value.

The adjustment module 403 is further configured to select target values from various temperature values and/or the impedance values to update extreme values of the preset range according to the various temperature values and/or the impedance values detected in real time in the preset period of time and a preset selection algorithm.

The adjustment module 403 is further configured to acquire historical radio frequency operation data corresponding to the task and object of the radio frequency operation; and determine the output power value of the radio frequency signals in the historical radio frequency operation data as the set power data. The set power data is a change trend curve representing the corresponding relationship between the radio frequency operation time and the output power.

The adjustment module 403 is further configured to acquire the output power value corresponding to the operation time in the period of the present radio frequency operation, and set the acquired output power value as the output power of the radio frequency signals.

The output module 401 is further configured to acquire the set power data from an externally connected removable memory, or acquire the set power data inputted from an input device. The set power data is a numerical range including a maximum value of the set power and a minimum value of the set power.

The output module 401 is further configured to set a median value of the numerical range as the output power of the radio frequency signals.

In the embodiment of the present disclosure, set power data corresponding to a radio frequency operation is acquired, an output power of the radio frequency signals is set according to the set power data, and then the radio frequency signals are outputted. The temperature value and/or the impedance value of the object of the radio frequency operation are detected in real time during the radio frequency operation, and whether the temperature value and/or the impedance value exceeds a preset range is determined. A power adjustment algorithm is determined according to the type of the radio frequency probe when the temperature value and/or the impedance value exceeds the preset range, and a target power value is calculated according to the power adjustment algorithm. If the temperature value or the impedance value is greater than the maximum value of the preset range, the output power of the radio frequency signals is reduced to the target power value, to reduce the risk of the radio frequency operation damaging the object and improve the safety of the radio frequency operation. If the temperature value or the impedance value is less than the minimum value of the preset range, the output power of the radio frequency signals is increased to the target power value, to improve the effect of the radio frequency operation. Further, if the temperature value and/or the impedance value does not exceed the preset range, the preset range of the temperature value and/or the impedance value is adjusted, improving the reasonableness of the preset range by automatically updating the preset range, to provide a more accurate data basis for subsequent radio frequency operations, and improve the reasonableness and success rate of the radio frequency operation.

Figure 5:
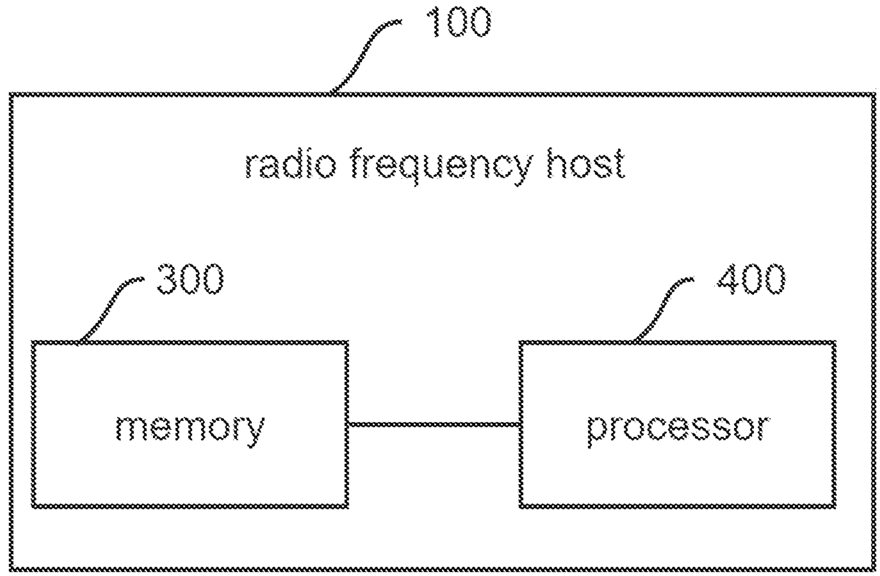
FIG. 5 is a schematic diagram showing a hardware structure in a radio frequency host according to an embodiment of the present disclosure.

Further, as shown in FIG. 5, an embodiment of the present disclosure further provides a radio frequency host, which includes a memory 300 and a processor 400. The processor 400 may be a central processor in the radio frequency host according to the above embodiments. The memory 300 is, for example, a hard drive memory, a non-volatile memory (such as flash memory or other electronically programmable limited-erasable memory for forming solid-state drive, etc.), and a volatile memory (such as static or dynamic random access memory), which is not limited in the embodiments of the present disclosure.

The memory 300 stores executable program codes; and the processor 400 is coupled to the memory 300 and configured to invoke the executable program codes stored in the memory, and implement the data adjustment method in a radio frequency operation as described above.

Further, an embodiment of the present disclosure further provides a computer-readable storage medium, which can be provided in the radio frequency host in the above embodiments, and may be the memory 300 in the embodiment shown in FIG. 5. A computer program is stored in the computer-readable storage medium, and when the program is executed by the processor, the data adjustment method in a radio frequency operation according to the embodiments shown in FIG. 2 and FIG. 3 is implemented. Further, the computer-readable storage medium may alternatively be a U disk, a movable hard disk, a read-only memory (ROM), RAM, a magnetic disk, an optical disc and other media that can store program codes.

The above embodiments are described from different aspects, and aspects of some embodiments that are not described in detail can refer to relevant aspects of other embodiments that are described in detail.

The data adjustment method in radio frequency operation and the radio frequency host provided in the present invention have been described above. Changes can be made to the specific implementation and the scope of application by those skilled in the art according to the concept of the embodiments of the present invention. Therefore, the disclosure of this specification should not be construed as a limitation of the present invention.

The invention claimed is:

1. A data adjustment method in a radio frequency operation, wherein an implementation body of the data adjustment method is a radio frequency host, the radio frequency host comprises a radio frequency probe, and the radio frequency host acts on an object of a present radio frequency operation via the radio frequency probe, and wherein the data adjustment method comprises steps of:

providing, by the radio frequency host, radio frequency signals with a preset power value, and outputting, by the radio frequency host, the radio frequency signals to the object of the present radio frequency operation via the radio frequency probe;

detecting, by the radio frequency host, physical characteristic data of the object of the present radio frequency operation in real time, and determining, by the radio frequency host, whether the physical characteristic data exceeds a preset range; and when the physical characteristic data exceeds the preset range, determining, by the radio frequency host, a power adjustment algorithm according to a type of the radio frequency probe, calculating, by the radio frequency host, a target power value according to the power adjustment algorithm, and adjusting, by the radio frequency host, the radio frequency output power to the target power value; and when the physical characteristic data does not exceed the preset range, adjusting, by the radio frequency host, the preset range according to the physical characteristic data detected in real time in a preset period of time before a present moment, wherein the step of determining, by the radio frequency host, the power adjustment algorithm according to the type of the radio frequency probe comprises:

when the type of the radio frequency probe is a single-electrode radio frequency probe, the power adjustment algorithm is to obtain the target power value by querying a preset corresponding relationship between a power adjustment amount and a variation of the physical characteristic data; and when the type of the radio frequency probe is a multi-electrode radio frequency probe, the power adjustment algorithm is a preset PID algorithm, by which the target power value is calculated.

2. The method according to claim 1, wherein the step of detecting, by the radio frequency host, the physical characteristic data of the object of the present radio frequency operation in real time comprises:

detecting, by the radio frequency host, temperature value of the object in real time.

3. The method according to claim 2, wherein the variation of the physical characteristic data is an adjustment value of the temperature value of the object; and the step of calculating, by the radio frequency host, the target power value according to the power adjustment algorithm and adjusting, by the radio frequency host, the radio frequency output power to the target power value comprises:

when the temperature value of the object detected in real time exceeds the preset range, determining, by the radio frequency host, a target value in the preset range, calculating, by the radio frequency host, the adjustment value of the temperature value according to the target value and the temperature value, and querying, by the radio frequency host, the corresponding relationship between the power adjustment value and the adjustment value of the temperature value, to obtain the power adjustment value;

when the temperature value is greater than the maximum value of the preset range, subtracting, by the radio frequency host, the power adjustment value from the preset power value to obtain a first target power value, and reducing, by the radio frequency host, the radio frequency output power to the first target power value; and when the temperature value is less than the minimum value of the preset range, adding, by the radio frequency host, the preset power value with the power adjustment amount to obtain a second target power value, and increasing, by the radio frequency host, the radio frequency output power to the second target power value.

4. The method according to claim 3, wherein the step of calculating, by the radio frequency host, the target power value according to the power adjustment algorithm and adjusting, by the radio frequency host, the radio frequency output power to the target power value comprises:

determining, by the radio frequency host, if the temperature value of the object detected in real time is greater than the maximum value of the preset range, a total to-be-set power, according to the minimum impedance of electrodes of the multi-electrode radio frequency probe;

detecting, by the radio frequency host, a real-time total power of the radio frequency probe, calculating, by the radio frequency host, the power adjustment value by preset PID algorithm according to the total to-be-set power and the real-time total power, and calculating, by the radio frequency host, the target power value according to the power adjustment value and the present output power of the radio frequency signals; and reducing, by the radio frequency host, the radio frequency output power to the target power value.

5. The method according to claim 1, wherein the step of adjusting, by the radio frequency host, the preset range according to the physical characteristic data detected in real time in the preset period of time before the present moment comprises:

selecting, by the radio frequency host, target values from various temperature values to update extreme values of the preset range according to the various temperature values detected in real time in the preset period of time and a preset selection algorithm.

6. The method according to claim 1, wherein the step of providing, by the radio frequency host, the radio frequency signals with the preset power value comprises:

acquiring, by the radio frequency host, historical radio frequency operation data corresponding to a task and the object of the radio frequency operation;

determining, by the radio frequency host, a output power value of the radio frequency signals in the historical radio frequency operation data as the set power data, wherein the set power data is a change trend curve representing a corresponding relationship between a radio frequency operation time and the output power;

acquiring, by the radio frequency host, the output power value corresponding to an operation time in the period of the present radio frequency operation from the change trend curve, and setting, by the radio frequency host, the acquired output power value as the preset power value.

7. The method according to claim 1, wherein the step of providing, by the radio frequency host, the radio frequency signals with the preset power value comprises:

acquiring, by the radio frequency host, the set power data from an externally connected removable memory, or acquiring, by the radio frequency host, the set power data inputted from an input device, wherein the set power data is a numerical range comprising a maximum value of the set power and a minimum value of the set power.

8. A radio frequency host, comprising:

an output module, configured to provide radio frequency signals with a preset power value, and output the radio frequency signals to a radio frequency probe;

a detection module, configured to detect physical characteristic data of an object of a present radio frequency operation in real time, and determine whether the physical characteristic data exceeds a preset range; and an adjustment module, configured to determine a power adjustment algorithm according to a type of the radio frequency probe, calculate a target power value according to the power adjustment algorithm, and adjust the radio frequency output power to the target power value when the physical characteristic data exceeds the preset range, wherein the adjustment module is further configured to adjust, when the physical characteristic data does not exceed the preset range, the preset range according to the physical characteristic data detected in real time in a preset period of time before a present moment, wherein when the type of the radio frequency probe is a single-electrode radio frequency probe, the power adjustment algorithm is to obtain the target power value by querying a preset corresponding relationship between a power adjustment amount and a variation of the physical characteristic data; and when the type of the radio frequency probe is a multi-electrode radio frequency probe, the power adjustment algorithm is a preset PID algorithm, by which the target power value is calculated.

9. A radio frequency host, comprising:

a non-transitory memory and a processor, wherein the non-transitory memory stores executable program codes; and the processor is coupled to the non-transitory memory, and configured to invoke the executable program codes stored in the non-transitory memory, and implement the data adjustment method in a radio frequency operation according to claim 1.

10. The method according to claim 1, wherein the step of detecting, by the radio frequency host, the physical characteristic data of the object of the present radio frequency operation in real time comprises:

detecting, by the radio frequency host, impedance value of the object in real time.

11. The method according to claim 10, wherein the variation of the physical characteristic data is an adjustment value of the impedance value of the object; and the step of calculating, by the radio frequency host, the target power value according to the power adjustment algorithm and adjusting, by the radio frequency host, the radio frequency output power to the target power value comprises:

when the impedance value of the object detected in real time exceeds the preset range, determining, by the radio frequency host, a target value in the preset range, calculating, by the radio frequency host, the adjustment value of the impedance value according to the target value and the impedance value, and querying, by the radio frequency host, the corresponding relationship between the power adjustment value and the adjustment value of the impedance value, to obtain the power adjustment value;

when the impedance value is greater than the maximum value of the preset range, subtracting, by the radio frequency host, the power adjustment value from the preset power value to obtain a first target power value, and reducing, by the radio frequency host, the radio frequency output power to the first target power value; and when the impedance value is less than the minimum value of the preset range, adding, by the radio frequency host, the preset power value with the power adjustment amount to obtain a second target power value, and increasing, by the radio frequency host, the radio frequency output power to the second target power value.

12. The method according to claim 11, wherein the step of calculating, by the radio frequency host, the target power value according to the power adjustment algorithm and adjusting, by the radio frequency host, the radio frequency output power to the target power value comprises:

determining, by the radio frequency host, if the impedance value of the object detected in real time is greater than the maximum value of the preset range, a total to-be-set power, according to the minimum impedance of electrodes of the multi-electrode radio frequency probe;

detecting, by the radio frequency host, a real-time total power of the radio frequency probe, calculating, by the radio frequency host, the power adjustment value by preset PID algorithm according to the total to-be-set power and the real-time total power, and calculating, by the radio frequency host, the target power value according to the power adjustment value and the present output power of the radio frequency signals; and reducing, by the radio frequency host, the radio frequency output power to the target power value.

13. The method according to claim 1, wherein the step of detecting, by the radio frequency host, the physical characteristic data of the object of the present radio frequency operation in real time comprises:

detecting, by the radio frequency host, temperature value and impedance value of the object in real time.

14. The method according to claim 13, wherein the variation of the physical characteristic data is an adjustment value of the temperature value and the impedance value of the object; and the step of calculating, by the radio frequency host, the target power value according to the power adjustment algorithm and adjusting, by the radio frequency host, the radio frequency output power to the target power value comprises:

when the temperature value and the impedance value of the object detected in real time exceeds the preset range, determining, by the radio frequency host, a target value in the preset range, calculating, by the radio frequency host, the adjustment value of the temperature value and the impedance value according to the target value and the temperature value and the impedance value, and querying, by the radio frequency host, the corresponding relationship between the power adjustment value and the adjustment value of the temperature value and the impedance value, to obtain the power adjustment value;

when the temperature value and the impedance value is greater than the maximum value of the preset range, subtracting, by the radio frequency host, the power adjustment value from the preset power value to obtain a first target power value, and reducing, by the radio frequency host, the radio frequency output power to the first target power value; and when the temperature value and the impedance value is less than the minimum value of the preset range, adding, by the radio frequency host, the preset power value with the power adjustment amount to obtain a second target power value, and increasing, by the radio frequency host, the radio frequency output power to the second target power value.

15. The method according to claim 14, wherein the step of calculating, by the radio frequency host, the target power value according to the power adjustment algorithm and adjusting, by the radio frequency host, the radio frequency output power to the target power value comprises:

determining, by the radio frequency host, if the temperature value and the impedance value of the object detected in real time is greater than the maximum value of the preset range, a total to-be-set power, according to the minimum impedance of electrodes of the multi-electrode radio frequency probe;

detecting, by the radio frequency host, a real-time total power of the radio frequency probe, calculating, by the radio frequency host, the power adjustment value by preset PID algorithm according to the total to-be-set power and the real-time total power, and calculating, by the radio frequency host, the target power value according to the power adjustment value and the present output power of the radio frequency signals; and reducing, by the radio frequency host, the radio frequency output power to the target power value.

16. The method according to claim 1, wherein the step of adjusting, by the radio frequency host, the preset range according to the physical characteristic data detected in real time in the preset period of time before the present moment comprises:

selecting, by the radio frequency host, target values from various impedance values to update extreme values of the preset range according to the various impedance values detected in real time in the preset period of time and a preset selection algorithm.

17. The method according to claim 1, wherein the step of adjusting, by the radio frequency host, the preset range according to the physical characteristic data detected in real time in the preset period of time before the present moment comprises:

selecting, by the radio frequency host, target values from various temperature values and impedance values to update extreme values of the preset range according to the various temperature values and impedance values detected in real time in the preset period of time and a preset selection algorithm.

* * * * *